US008697140B2

(12) United States Patent
Arndt et al.

(10) Patent No.: US 8,697,140 B2
(45) Date of Patent: Apr. 15, 2014

(54) VIRUCIDAL DISINFECTANT

(75) Inventors: Andreas Arndt, Lucerne (CH); Olga Willi, Notwil (CH)

(73) Assignee: B. Braun Medical AG, Emmenbrücke (CH)

( * ) Notice: Subject to any disclaimer, the term of this patent is extended or adjusted under 35 U.S.C. 154(b) by 321 days.

(21) Appl. No.: 12/473,715

(22) Filed: May 28, 2009

(65) Prior Publication Data
US 2009/0252775 A1 Oct. 8, 2009

Related U.S. Application Data

(63) Continuation of application No. 11/341,737, filed on Jan. 27, 2006, now abandoned.

(30) Foreign Application Priority Data

Jan. 28, 2005 (EP) .................................. 05100562

(51) Int. Cl.
*A61K 33/42* (2006.01)
*A01N 25/34* (2006.01)
*A01N 25/08* (2006.01)

(52) U.S. Cl.
USPC ........................... 424/605; 424/402; 424/409

(58) Field of Classification Search
None
See application file for complete search history.

(56) References Cited

U.S. PATENT DOCUMENTS

| | | | | | |
|---|---|---|---|---|---|
| 4,167,583 | A | * | 9/1979 | Knott et al. .................... | 514/730 |
| 4,329,336 | A | * | 5/1982 | Su et al. ....................... | 424/70.17 |
| 5,260,021 | A | * | 11/1993 | Zeleznick ....................... | 422/28 |
| 5,622,708 | A | | 4/1997 | Richter et al. | |
| 5,792,733 | A | * | 8/1998 | Minami et al. ................ | 508/422 |
| 6,080,417 | A | | 6/2000 | Kramer et al. | |
| 6,224,827 | B1 | * | 5/2001 | Lembke ........................ | 422/28 |
| 6,346,279 | B1 | * | 2/2002 | Rochon .......................... | 424/616 |
| 6,982,069 | B2 | | 1/2006 | Tanaka et al. | |
| 2002/0137631 | A1 | | 9/2002 | Falder et al. | |
| 2002/0192297 | A1 | | 12/2002 | Ramirez et al. | |
| 2004/0146479 | A1 | * | 7/2004 | Kritzler ...................... | 424/70.27 |
| 2005/0113276 | A1 | | 5/2005 | Taylor et al. | |

FOREIGN PATENT DOCUMENTS

| | | |
|---|---|---|
| DE | 196 12 057 | 2/1997 |
| DE | 19603977 | 8/1997 |
| EP | 0 381 617 | 8/1990 |
| EP | 0 689 767 A2 | 1/1996 |
| EP | 0940145 | 9/1999 |
| JP | 63 305872 | 12/1988 |
| JP | 2004-189613 | 7/2004 |
| WO | WO 86/05391 | 9/1986 |
| WO | WO 90/06677 | 6/1990 |
| WO | WO 95/02393 | 1/1995 |
| WO | WO 0013507 | 3/2000 |
| WO | WO0013507 | * 3/2000 |
| WO | WO 0024851 | 5/2000 |
| WO | WO0024851 | * 5/2000 |
| WO | WO 2005/051342 | 6/2005 |

OTHER PUBLICATIONS

Definition of Germ by the free Online dictionary.*
Definition of Germ by the free Online medical dictionary.*
Boubakar B. BA, et al., Separation Methods for Antiviral Phosphorous-Containing Drugs, Journal of Chromatography B, Nov. 25, 2001, pp. 349-362, Elsevier Science Publishers.
Int'l Search Report for EP 06100915, dated May 10, 2006.
English Translation of Third Party Challenge in EP 06100910, dated Sep. 29, 2008.
English Translation of Examination in EP Application 06100910, dated Dec. 3, 2008.
Observations by Third Parties pursuant to Article 115 EPC submitted Feb. 18, 2010, in EP 1685854A1 (and translation).
Response to EPO Official Action of Mar. 2, 2007, submitted Nov. 5, 2007, in EP 1685854A1 (and translation).
Response to EPO Offficial Action of Dec. 3, 2008, submitted Jun. 8, 2009, in EP 1685854A1 (and translation).
Safety Data Sheet of Manorapid Synergy (no translation).
Opposition Filed in European Application No. 06.100915.5, Jul. 11, 2011 (w/English language machine translation).
Product Description Manarapid ® Synergy-"viruzides" Handedesinfektionsmittel (not available in English language).
Rudolph, et al., *"Developing an Effective Virucidal Hand Disinfectant based on a Synergetic Combination of Selected Alcohols"*.
Kramer, *"Trends und Entwicklungen in der Desinfektion-Schwerpunkt Hände"* (not available in English language); Sep. 24, 2003.
Kramer, Handout for lecture *"Handedesinfektion and Virus Inactivation"*; Institute for Hygiene und Umweltmedizin Greifswald; Nov. 30, 2000 (not available in English language).
Steinmann, Expert Statement *"Efficacy of Adenovirus MANORAPID Synergy in a quantitative suspension test at 20° C."*; Dec. 15, 2004 (w/English language summary).
Extract from the International Cosmetic Ingredient Dictionary and handbook, 7m Edition (1997).
Rheinbaben et al, Excerpt from Handbook of Virus-Effective Disinfection, 1 Edition (Dec. 2001(not available in English language)).
Internet Expression "disinfection 3" (1997(not available in English language)).

* cited by examiner

*Primary Examiner* — David J Blanchard
*Assistant Examiner* — Tigabu Kassa
(74) *Attorney, Agent, or Firm* — RatnerPrestia

(57) ABSTRACT

A virucidal disinfectant having broad-range activity includes an acidic phosphorus compound and/or salt thereof, an alcohol, and one or more polyalkylene glycols. The disinfectant, which may also kill bacteria and/or fungi, may be used for the hygienic disinfection of animate and inanimate surfaces. The invention also provides a disinfection method and a product containing a disinfectant.

31 Claims, No Drawings

VIRUCIDAL DISINFECTANT

CROSS REFERENCE TO RELATED APPLICATIONS

This application is a continuation application of U.S. application Ser. No. 11/341,737, abandoned, filed Jan. 27, 2006, the content of such application being incorporated by reference herein. This patent application claims priority of European patent application number 05100562.7, filed Jan. 28, 2005, the entire disclosure of which is incorporated herein by reference.

BACKGROUND OF THE INVENTION

The present invention relates to a virucidal disinfectant having broad-range activity, the use of said disinfectant for the hygienic disinfection of animate and inanimate surfaces as well as for killing viruses, bacteria and fungi.

Further, the invention relates to a disinfection method and to a product containing a disinfectant.

In recent years, disinfectants have gained importance. Of particular importance is the use of disinfectants in field such as hospitals, medical practices, old-age homes, emergency wards, but also in factories which are not related with medical aid, such as food-producing factories, in the pharmaceutical branch and in further branches in which working under clean room conditions is necessary. Particularly important in these fields is the disinfection of hands, because the latter are often responsible for the communication of all kinds of pathogens.

The disinfection of hands is an established method for preventing the transmission of infections. For this purpose, alcohol-based products for rubbing are used today according to the prior art. This principle has been known for about 30 years. The preparations employed are usually based on the active substances ethanol, propane-1-ol, propane-2-ol and mixtures of the mentioned alcohols.

With the known commercially available preparations, which have an alcohol content of 60% and more, it is possible to reduce the transient germ flora of the hands efficiently within 30 seconds.

The mentioned alcohols and their mixtures as well as many commercially available preparations are able to inactivate enveloped viruses. However, if a comprehensive antiviral effectiveness is required, the alcohols as well as the preparations known to the skilled person have a number of drawbacks. Thus, it is known that ethanol is effective against enveloped and non-enveloped viruses only in high concentrations. In contrast, propane-1-ol and propane-2-ol are only selectively effective; they are ineffective against most non-enveloped viruses, e.g., against the highly resistant picornaviruses, which include polioviruses and hepatitis A virus.

In the past, several attempts were made for enhancing the effectiveness of alcoholic rubbing preparations against viruses. As a result, some preparations are known for which virucidal effectiveness is stated.

U.S. published patent application No. 2004/0146479 A1 describes compositions for hand disinfection. An exemplary composition contains 55% (w/v) of ethanol (70% v/v), 0.1% (w/v) of phosphoric acid, 6% (w/v) of polyethylene glycol (400), 2% (w/v) of polyethylene glycol (4000), 0.50% (w/v) of propylene glycol and 0.35% (w/v) of benzyl alcohol.

The European Unexamined Patent Application EP-A2-0 556 546 describe agents which are characterized by containing at least 60% of at least one alcohol as well as at least one Lewis acid. As Lewis acids, salts of aluminum or zinc are mentioned, the chlorohydrates and chlorides being particularly pointed out. The products are supposed to have effectiveness against poliovirus type 1 strain Mahoney. Chlorides are known to have corrosive properties, which is also referred to as chloride-induced pitting. The disclosure of German Offenlegungsschrift DE-A1-4205828 is to be evaluated in similar terms.

The European Unexamined Patent Application EP-A2-0 176 720 describes agents which contain at least 70% methanol and/or ethanol, from 1 to 10% glycerol and from 0.5 to 5% castor oil and are suitable for inactivating non-enveloped viruses. The demonstration has been effected exclusively with the wild type poliovirus type 1 Mahoney.

The European Unexamined Patent Application EP-A2-0 251 303 discloses a virucidal agent which contains at least 70% ethanol and a short-chain acid. The agent can additionally contain glycerol and castor oil. The application properties of such products have proven non-optimum due to the sticky skin feeling after the application.

The German Offenlegungsschrift DE-A1-4221743 describes agents which contain a lower alcohol as well as the salt of a lower carboxylic acid. Products formulated on the basis of this teaching have proven non-effective against papoviruses, even if the time of action was extended to 10 minutes.

A commercially available preparation contains 32.251 g of propan-1-ol, 20.985 g of propan-2-ol, 4.2 g of 20% chlorohexidine digluconate solution, 1-tetradecanol, Macrogol 4000, cetearyl octanoate, patent blue V, perfumes and purified water. According to the manufacturer, this preparation is effective against vaccinia viruses, rotaviruses, hepatitis B viruses, hepatitis C viruses and human immunodeficiency viruses (HIV).

A preparation obtainable in the Federal Republic of Germany contains 95% ethanol as a basic active ingredient as well as denaturing agents and skin-care substances. In the list of the Robert Koch Institute (RKI), the product is rated as effective against viruses. According to the manufacturer, its required time of action is 2 minutes. The required time of action against papoviruses and adenoviruses determines the effectiveness. Against polioviruses, the preparation is effective within 60 seconds. The preparation is insufficiently effective against parvoviruses. According to the manufacturer, the flash point of the preparation is 0° C. The storage and shipping of such a preparation are correspondingly demanding.

The German Patent Specification DE-C1-4424325 and the European Unexamined Patent Application EP-A1-0 692 192 describe an alcoholic disinfectant formulation having a content of ethanol and/or methanol of at least 80 percent by weight, which is characterized by containing butanone. The formulation may contain chlorohexidine or benzalkonium chloride as remanent active ingredients. The formulation may contain an alkylene glycol, namely triethylene glycol or glycerol, as well as an ester of a long-chain fatty acid as care substances. The disinfectant formulation is claimed for the inactivation of non-enveloped viruses, especially polioviruses.

The German Offenlegungsschrift DE-A1-19962353 describes a hepatitis A virucidal agent which contains one or more alcohols and up to 0.5% of a chlorine-containing or chlorine-releasing agent. The agent may further contain up to 10% of antimicrobial acids, such as undecylenic acid, citric acid, p-hydroxybenzoic acid, sorbic acid, salicylic acid. A commercially available preparation contains 90% ethanol, 0.20% chlorohexidine gluconate and further additives. This preparation is evidently based on the German Patent Specification DE-C1-4424325 and/or the German Offenlegungsschrift DE-A1-19962353. The commercially available preparation has a low flash point, which is stated by the manufacturer to be 15° C. An effectiveness of this preparation against papovaviruses is not known.

The Published International Patent Application WO-A1 97/35475 discloses a product having a flash point of above 21° C. which contains lower alcohols and synergists. As synergists, diols, especially propylene glycol, butylene glycol and their mixtures, are employed. The product may contain a physiologically acceptable organic acid. A commercial product which is based on this patent specification contains 54.1% ethanol, 10% 1-propanol, 5.90% propane-1,2-diol and 5.7% butane-1,3-diol. For short-term application, the product seems to be suitable for hand disinfection. However, when used continuously, the high content of non-volatile diols proves to be disturbing, because these diols remain on the hands as a residue and can cause an uncomfortable skin feeling. Especially for application for hand disinfection in surgery, preparations according to WO-A1-97/35475 have limited suitability.

The European Unexamined Patent Application EP-A1-0 848 907 claims a spray disinfectant which contains from 30 to 70% of ethanol, an amine component and a terpene hydrocarbon. Using it, preparations having activity against polioviruses can be formulated. However, due to their composition, products of this type can be employed only for the disinfection of inanimate surfaces.

The German Offenlegungsschrift DE-A1-10237227 describes an alcoholic hand and skin disinfectant with ascorbic acid and/or its degradation products, which is supposed to have improved activity against poliovirus type 1 strain Mahoney and adenovirus strain adenoid 6. One of its degradation products is oxalic acid, which not physiologically acceptable.

Peracids are known to exhibit activity against bacteria and viruses, so that it appears obvious to employ peracids also for the disinfection of hands. In this connection, the RKI list states a preparation based on diluted aqueous peracetic acid, which has not been rated "effective against viruses", however.

The German Offenlegungsschrift DE-A1-19724102 describes agents for rapid disinfection or decontamination comprising a content of physiologically acceptable peracids. It is not known whether this product is also effective against viruses. Irrespective thereof, it is difficult to handle, and the stability of the ready-to-use solutions to be employed is limited.

The German Offenlegungsschrift DE-A1-10106444 claims agents for virucidal hand disinfection which are prepared from components A and B, wherein component A consists of from 50 to 80% of a liquid aliphatic alcohol or mixtures of liquid aliphatic alcohols, and component B comprises a 20% to 30% solution of glycerol monoperacetate diacetate and/or glycerol monoperacetate acetate and/or glycol monoperacetate acetate and urea. Components A and B must be combined in a dosing and mixing device. Components A and B are supposed to be stable, but the mixture of components A and B is not storage-stable over an extended period of time. In addition, the mixing of the components requires a higher logistic expenditure, for example, in order to guard against the risk of confusion of the components. Also, the dosing and mixing device is to be designed to avoid the premature consumption of one of the components at any rate.

Inorganic acids mostly have a limited effectiveness against viruses. In the Handbuch der Viruswirksamen Desinfektion (ISBN 3-540-67532-9), published by the Springer Verlag, Berlin, Heidelberg, New York, in 2002, the authors point out on page 79 that some viruses which have to pass the stomach in the course of their infection path are fairly resistant against acids. The authors stress the point that phosphoric acid is still ineffective against poliovirus in a concentration as high as 3%.

In the past, the Deutsche Gesellschaft für Hygiene und Mikrobiologie (DGHM) declared preparations for instrument disinfection as virucidal in their list if an activity against the poliovirus type 1 strain Mahoney could be detected. However, a general virucidal property cannot be concluded from the activity against poliovirus alone. On the other hand, it is neither possible nor reasonable to intend to test the activity against all known viruses individually. Currently, this is not possible for mere methodic reasons, because no possibility of in vitro growth has been found as yet for a number of viruses in spite of the advanced technical progress.

Therefore, when virucidal property is established, it has been found appropriate to establish the effectiveness by means of selected critical model viruses in order to conclude to a general virucidal property on the basis of such results. This approach is supported by the Directions of the German Federal Public Health Administration and the Deutsche Vereinigung zur Bekämpfung der Viruskrankheiten of 1982.

These Directions have been updated by the Comment, issued in 2004, of the Working Group Virucidal Property of the Robert Koch Institute (RKI) and the Specialist Panel "Virus disinfection" of the Deutsche Gesellschaft zur Bekämpfung der Viruskrankheiten (DVV) and the Disinfectant Commission of the Deutsche Gesellschaft für Hygiene und Mikrobiologie (DGHM).

In this Comment, the testing and declaration of effectiveness of disinfectants against viruses is newly settled in the form of an RKI Recommendation. This RKI Recommendation has appeared in the technical journal Bundesgesundheitsblatt—Gesundheitsforschung—Gesundheitsschutz 2004, 47, pp. 62-66. In the following text, this Recommendation is shortly referred to as "RKI Virucidal Property Recommendation".

According to this RKI Virucidal Property Recommendation, preparations claiming virucidal effectiveness are tested in the Federal Republic of Germany against the following model viruses: adenovirus type 5 (strain Adenoid 75), papovavirus [simian virus 40 (SV40), strain 777], poliovirus (polio vaccination strain type I, strain LSc-2ab), vaccinia virus (strain Elstree). A preparation is considered effective against the respective test virus if a reduction of the virus titer of at least 4 logarithmic steps is achieved in a quantitative suspension experiment.

In the testing for virucidal property, 8 parts of product, 1 part of virus suspension and 1 part of load substance or water are mixed. Due to methodic conditions, this results in an 80% concentration of the test preparation. The test preparations are examined without a load, with a load of 0.2% bovine albumin and with a load of 10% fetal calf serum. Only a preparation which achieves a reduction of the virus titer of at least 4 logarithmic steps under all test conditions meets the conditions of the RKI with respect to antiviral effectiveness. In the European Testing Standard EN 14476, which describes the quantitative suspension experiment for virucidal property in human medicine, it is noted under item 1 that a disinfectant or antiseptic agent which is used neat must be tested in 80% concentration.

If a test preparation fails to reach the required effectiveness against the test virus, it has become established that the manufacturer concentrates his product by dispensing with part of the water normally contained in his formulation, and a thus especially processed preparation is again tested at a higher concentration. Thus, in the literature, statements about test preparations can be found in which, although antiviral effectiveness within 1 to 2 minutes is stated, the concentration of the test preparations is documented as being, for example, 90%, 94% or 100%. Strictly speaking, this is a deviation from the standard test conditions, and such preparations are thus not really to be rated as virucidal in accordance with the RKI Virucidal Property Recommendation and the European Testing Standard EN 14476. In addition, the objective mutual comparability of the preparations is rendered more difficult.

If the Directions of the Federal Public Health Administration and the Deutsche Vereinigung zur Bekämpfung der Viruskrankheiten of 1982 are compared with the current RKI Virucidal Property Recommendation, it strikes that individual test viruses have been changed for methodic reasons. Thus, the wild type poliovirus type 1, strain Mahoney, was used formerly instead of the vaccination strain type I, strain LSc-2ab. A similar situation holds for the adenovirus, in which case the strain Adenoid 6 was used formerly. The changes in the viral strains yielded interesting results. A slightly modified product based on the active ingredients 78.2% of 96% ethanol and 10% of 2-propanol, which had achieved effectiveness against the poliovirus type 1 strain Mahoney within 2 minutes, proved to be insufficiently effective against the poliovirus vaccination strain type I, strain LSc-2ab. Therefore, it is to be doubted whether the results established in the past relating to the effectiveness of preparations towards the poliovirus type 1 strain Mahoney can be generally transferred to the poliovirus vaccination strain type I, strain LSc-2ab.

Another problem is seen in the practice of hand disinfection. As a rule, medical institutions have several preparations on store nowadays: one product for routine disinfection and another preparation to be applied especially for exposure to unknown viruses. The logistic problems resulting therefrom and the high demands on personnel training are a challenge which is not to be underestimated.

It is noted that today there is still a need for improved disinfectants, especially hand disinfectants, with virucidal effectiveness, especially for those which have a broad-range activity and are suitable both for routine use and for exposure to unknown viruses.

SUMMARY OF THE INVENTION

In one aspect, the invention provides a virucidal disinfectant having broad-range activity. The disinfectant includes
a) one or more acidic phosphorus compounds selected from the group consisting of phosphoric acid, diphosphoric acid, triphosphoric acid, polyphosphoric acid of general formula $H_{n+2}P_nO_{3n+1}$, where n is an integer of from 1 to 17, cyclotri- and cyclotetrametaphosphoric acids, polymetaphosphoric acid, peroxomonophosphoric acid, peroxodiphosphoric acid, hypophosphoric acid, diphosphoric(III,IV) acid, and salts of these acids;
b) an alcohol component selected from the group consisting of ethanol, propane-1-ol, propane-2-ol, and mixtures of any of these; and
c) one or more polyalkylene glycols.
The one or more acidic phosphorus compounds constitute from 0.2 to 1.5% by weight of the disinfectant.

In another aspect, the invention provides a method of killing a pathogen that includes contacting the pathogen with the above disinfectant.

In yet another aspect, the invention provides a product that includes a disinfectant as described above and means for dispensing the disinfectant.

DETAILED DESCRIPTION OF THE INVENTION

The present invention provides disinfectants having high effectiveness against viruses, bacteria and/or fungi, and which are typically well tolerated upon contact with human skin in continuous use.

Surprisingly, it has now been found that virucidal disinfectants which contain phosphorus compounds, alcoholic components and polyalkylene glycol meet the above mentioned requirements.

Therefore, in a first general embodiment, the present invention relates to a virucidal disinfectant having broad-range activity which contains:
a) one or more phosphorus compounds;
b) one or more alcoholic components; and
c) one or more polyalkylene glycols.

The virucidal disinfectants according to the invention contain one or more phosphorus compounds as an essential component. Particularly suitable phosphorus compounds which may be employed in the disinfectants according to the invention include acidic phosphorus compounds and/or salts thereof. "Acidic phosphorus compounds" within the meaning of the present invention are phosphorus compounds which are capable of releasing protons in an aqueous medium (Brønstedt acids). It is particularly preferred to employ one or more acidic phosphorus compounds selected from the group consisting of phosphoric acid, diphosphoric acid, triphosphoric acid, polyphosphoric acid ($H_{n+2}P_nO_{3n+1}$, where n is an integer of from 1 to 17), cyclotri- and cyclotetrametaphosphoric acids, peroxomonophosphoric acid, peroxodiphosphoric acid, hypophosphoric acid, diphosphoric(III,IV) acid and salts of the above mentioned acids. The salts are preferably the alkali metal salts, especially the sodium and potassium salts, of the acidic phosphorus compounds mentioned.

In a preferred embodiment, the disinfectants according to the invention contain one or more acidic phosphorus compounds and/or a salt or salts of one or more acidic phosphorus compounds.

The acidic phosphorus compounds and their salts are not subject to any additional limitations. However, it is advantageous if both the acidic phosphorus compound and the salts of the acidic phosphorus compounds are soluble in the disinfectant compositions, which are preferably aqueous-alcoholic.

Particularly preferred is the use of phosphoric acid and/or one or more alkali metal salts of phosphoric acid. The use of phosphoric acid and/or sodium dihydrogenphosphate and/or potassium dihydrogenphosphate has proven particularly useful. In addition, it has been surprisingly found that skin tolerance could be significantly increased by mixtures of phosphoric acid with sodium dihydrogenphosphate and/or potassium dihydrogenphosphate. This is important, in particular, if the disinfectant is employed as a hand disinfectant.

Advantageously, one or more phosphorus compounds are employed in amounts of from 0.2 to 1.5 percent by weight, preferably from 0.2 to 1.0 percent by weight, especially from 0.2 to 0.8 percent by weight, respectively based on the total agent.

As a further essential component, the disinfectants according to the invention contain one or more polyalkylene glycols.

Polyalkylene glycols (polyglycols, polyglycol ethers; INCI chemical class: polymeric ethers) are known polyethers which are predominantly linear, but may also be branched in part, and which are polymers with terminal hydroxy groups. The polyalkylene glycols having higher molecular weights are polymolecular, i.e., they consist of collections of macromolecules having different molecular weights.

The average relative molecular weights of the polyalkylene glycols are preferably within a range of from 400 to 10,000, especially from 1000 to 8000, more preferably from 2000 to 6000, and most preferably from 3000 to 5000. In the different polyalkylene glycols described in the following, particular ranges may still be particularly advantageous.

Preferred according to the invention are linear or branched, especially linear, polyalkylene glycols of general formula HO—[R—O]$_n$—H, in which R represents $(CH_2)_2$, $CH_2CH(CH_3)$, $CH_2CH(CH_2CH_3)$ and/or $(CH_2)_4$, and n represents values or average values of from 2 to about 200, preferably from 3 to 190, more preferably from 4 to 180, still more preferably from 6 to 150, especially from 10 to 120. The polyalkylene glycols can be prepared by the ring-opening polymerization of ethylene oxide, propylene oxide and/or tetrahydrofuran. In particular, these are the polyethylene glycols with $R=(CH_2)_2$, the polypropylene glycols with $R=CH_2CH(CH_3)$, the polytetrahydrofurans with $R=(CH_2)_4$ and the copolymers of ethylene oxide, propylene oxide and/or tetrahydrofuran.

Preferred according to the invention are polyethylene glycols (PEG) having an average relative molecular weight of from 400 to 10,000, especially from 1000 to 8000, more preferably from 2000 to 6000 and most preferably from 3000 to 5000. For polyethylene glycols, there are different nomenclatures which may lead to confusion. In technical contexts, it is usual to state the average relative molecular weight after the designation "PEG", so that "PEG 200" characterizes a polyethylene glycol having a relative molecular weight of from about 190 to about 210. According to the INCI nomenclature, the abbreviation PEG is provided with a hyphen which is directly followed by a figure which corresponds to the number n in the above general formula. Commercially available polyethylene glycols are, for example, PEG 200/PEG-4, PEG 300/PEG-6, PEG-7, PEG-8, PEG 400, PEG-9, PEG-10, PEG-12, PEG 600, PEG-14, PEG-16, PEG 800/PEG-18, PEG-20, PEG 1000, PEG 1200, PEG 1500/PEG-32, PEG-40, PEG 2000, PEG-55, PEG-60, PEG 3000, PEG 3350/PEG-75 and PEG 4000/PEG-90, where the designations according to the two nomenclatures for the same polyethylene glycols are juxtaposed, separated by the slash ("/") sign. The commercially available polyethylene glycols are obtainable, for example, under the trade names Carbowax® (Union Carbide), Emkapol® and Renex® PEG (ICI), Lipoxol® (DEA), Polyglycol® E (Dow), Pluracol® E, Pluriol® E as well as Lutrol® E (BASF).

Polypropylene glycols (PPG) are clear and almost colorless liquids over a broad range of molecular weights from 250 (PPG-4) to 4,000 (PPG-69), and the above described INCI nomenclature is used in an analogous way to designate them. Thus, the polypropylene glycols of the above general formula with n values of 5 and 6 are referred to as PEG-5 and PEG-6, respectively. The low-molecular weight polypropylene glycols are miscible with water, while those of higher molecular weight are less soluble in water. For example, commercially available are the polypropylene glycols PPG-7, PPG-9, PPG-12, PPG-13, PPG-15, PPG-17, PPG-20, PPG-26, PPG-30, PPG-33, PPG-34, PPG-51 and PPG-69, as referred to in accordance with INCI. Supply sources can be seen in the International Cosmetic Ingredient Dictionary and Handbook.

The copolymers are preferably random copolymers and, in particular, block copolymers of ethylene and propylene oxides, ethylene oxide and tetrahydrofuran, propylene oxide and tetrahydrofuran, or ethylene oxide, propylene oxide and tetrahydrofuran, preferably copolymers of ethylene and propylene oxides, more preferably block copolymers of ethylene and propylene oxides.

Random copolymers of "a" ethylene oxide moieties and "b" propylene oxide moieties preferred according to the invention are, for example, the following copolymers referred to as PEG/PPG-a/b (molecular weight) in accordance with the International Cosmetic Ingredient Dictionary and Handbook, a and b being average values: PEG/PPG-18/4 copolymer (1000), PEG/PPG-17/6 copolymer (1100), PEG/PPG-35/9 copolymer (2100) and PEG/PPG-23/50 copolymer (3900).

Block copolymers of ethylene and propylene oxides preferred according to the invention are represented by the formula $HO(CH_2CH_2O)_x(CH(CH_3)CH_2O)_y(CH_2CH_2O)_{x'}H$, where x and x' represent average values of from 2 to 130, and y represents average values of from 15 to 67, and are designated with the international non-proprietary name Poloxamer, which is also used in the International Cosmetic Ingredient Dictionary and Handbook. Each Poloxamer is characterized by a three-digit number. The first two digits, when multiplied by 100, yield the average molecular weight of the polypropylene glycol fraction, and the last digit, when multiplied by 10, yields the polyethylene glycol fraction in % by weight. The latter is from 10 to 80% by weight, preferably not more than 50% by weight, especially not more than 40% by weight, more preferably not more than 30% by weight, for example, 10%, 20% or 30% by weight. The preparation of the Poloxamers is effected in two steps, wherein at first propylene oxide is added to propylene glycol in a controlled way, and the polypropylene glycol block obtained is flanked by two polyethylene glycol blocks by the subsequent addition of ethylene oxide. Particularly preferred block copolymers include, for example, the following liquid Poloxamer types (x, y, x'; molecular weight; melting point in part): Poloxamer 101 (2, 16, 2; 1100; −32), Poloxamer 122 (5, 21, 5; 1630; −26), Poloxamer 123 (7, 21, 7; 1900; −1), Poloxamer 105 (11, 16, 11; 1850; 7), Poloxamer 181 (3, 30, 3; 2000; −29), Poloxamer 124 (11, 21, 11; 2200; 16), Poloxamer 182 (8, 30, 8; 2500; −4), Poloxamer 183 (10, 30, 10; 2650; 10), Poloxamer 212 (8, 35, 8; 2750; −7), Poloxamer 231 (6, 39, 6; 2750; −37), Poloxamer 184 (13, 30, 13; 2900; 16), Poloxamer 185 (19, 30, 19; 3400), Poloxamer 282 (10, 47, 10; 3650; 7), Poloxamer 331 (7, 54, 7; 3800; −23), Poloxamer 234 (22, 39, 22; 4200; 18), Poloxamer 401 (6, 67, 6; 4400; 5), Poloxamer 284 (21, 47, 21; 4600) and Poloxamer 402 (13, 67, 13; 5000; 20). The Poloxamers are commercially available under the trade names Pluronic® and Synperonic® PE, followed by a letter from the group of L, P and F as well as a two- or three-digit number. The last digit is identical with the last digit of the Poloxamer nomenclature, and the preceding one- or two-digit numbers, when multiplied with 300, yield the approximate molecular weight of the polypropylene glycol fraction, or when multiplied by 3, approximately yield the number formed by the first two digits of the number of the Poloxamer nomenclature, i.e., 3, 4, 6, 7, 8, 9, 10 and 12 respectively correspond to the two-digit numbers 10, 12, 18, 21, 23, 28, 33 and 40 at the beginning of the figure according to the Poloxamer nomenclature. The letters distinguish between liquid (L), pasty (P) and solid (F) Poloxamers. Thus, for example, the Poloxamer 101 can be obtained as Pluronic® L 31 and Synperonic® PE L 31.

Another class of suitable block copolymers of ethylene and propylene oxides are represented by the formula $HO(CH(CH_3)CH_2O)_y(CH_2CH_2O)_x(CH_2CH(CH_3)O)_yH$. Here, one polyethylene glycol block is framed by two polypropylene glycol blocks, while in the Poloxamers, one polypropylene glycol block is flanked by two polyethylene glycol blocks. Their preparation is again effected in two steps, wherein at first ethylene oxide is added to ethylene glycol in a controlled way, and the polyethylene glycol block obtained is flanked by two polypropylene glycol blocks by the subsequent addition of propylene oxide. Like the Poloxamers, these block copolymers are commercially available under the trade name Pluronic® (BASF), respectively followed by an alphanumerical code of three digits and the letter R inserted between the second and third digits. The meanings of the digits is the same as in the Poloxamer nomenclature. The inserted letter R (for "reverse") indicates the inverted structure relative to that of the Poloxamers. Preferred representatives of this class are the following Pluronic® types (molecular weight; melting point): Pluronic® 10R5 (1950; 15), Pluronic® 12R3 (1800; −20), Pluronic® 17R1 (1900; −27), Pluronic® 17R2 (2150; −25), Pluronic® 17R4 (2650; 18), Pluronic® 25R1 (2700; −5), Pluronic® 25R2 (3100; −5), Pluronic® 31R1 (3250; −25) and Pluronic® 31R2 (3300; 9).

In a further preferred embodiment, one or more of the terminal hydroxy groups of the above mentioned alkylene glycols may additionally be etherified. In the preferred terminal etherified alkylene glycols, the hydrogen atoms of the hydroxy groups are replaced by linear or branched, saturated or unsaturated alkyl groups with from 1 to 30 carbon atoms.

The polyalkylene glycols are advantageously employed in an amount of from 0.05 to 8% by weight, preferably from 0.1 to 5% by weight, more preferably from 0.5 to 3% by weight, especially from 0.8 to 1.5% by weight, respectively based on the total agent.

The disinfectants according to the invention contain at least one alcoholic component as a further essential component. Aliphatic alcohols with a linear or branched alkyl group which bears from 1 to 6 carbon atoms are preferably employed. Preferably, the alcohols are monoalcohols. Particularly preferred are aliphatic alcohols with from 1 to 4, especially 2 or 3, carbon atoms. Particularly strongly virucidal disinfectants can be obtained if ethanol and/or propan-1-ol and/or propan-2-ol, preferably mixtures of ethanol and propanol-1-ol, are employed as alcoholic components.

It is just in the interplay with the acidic phosphorus compounds, especially phosphoric acid, that is has been surprisingly found that an excellent skin tolerance could be achieved with the alcoholic components in spite of the acidic pH value. This was surprising because alcoholic products which tend to an acidic pH value have always been rated as poorly skin tolerable to date.

In a preferred embodiment, the disinfectants according to the invention contain the alcoholic component in an amount of from 30 to 80% by weight, preferably from 45 to 80% by weight, especially from 60 to 75% by weight, respectively based on the total agent.

The pH value of the undiluted disinfectant is preferably within a range of from 3 to 7, more preferably from 3.5 to 6.5, especially from 4 to 6.

In a preferred embodiment, the disinfectant according to the invention has a flash point (measured according to DIN 51755) of at least 21° C. The high flash point of the disinfectant significantly facilitates its shipping and storage.

The disinfectants according to the invention are especially suitable for the disinfection of animate surfaces, such as skin and, in particular, hands. Therefore, it is advantageous that the disinfectants according to the invention additionally contain skin care components. These are preferably selected from the group consisting of glycerol, propane-1,2-diol, butane-1,3-diol, sorbitol, dexpanthenol, allantoin, bisabolol, tocopheryl acetate, dodecanol, tetradecanol, hexadecanol, octadecanol, lanolin alcohol, cetearyl alcohol, cyclomethicone, dimethicone, isopropyl myristate, isopropyl palmitate, cetearylethyl hexanoate, octyl stearate, octyl octanoate, ethylhexanoic acid ethyl ester, jojoba oil, sea buckthorn oil, wool wax, paraffin oil, vaseline, heptamethyinonane/isohexadecane, cholesterol, partial glycerides and triglycerides.

Preferably, the disinfectants according to the invention contain from 0.01 to 5% by weight, especially from 0.1 to 2% by weight, of one or more skin care components, respectively based on the total agent.

Especially if the disinfectants according to the invention are employed in continuous use, such as when using the disinfectant as a hand disinfectant in the clinical or pharmaceutical fields, the addition of refatting agents has proven particularly advantageous. Refatting agents prevent the skin which comes into contact with the disinfectants from drying out. Refatting agents render the skin soft and supple. Refatting agents are familiar to the skilled person. The refatting agents selected from the group consisting of glycerol tri-, di- and monooleate, glyceryl caprylate, glyceryl caprate, polyglyceryl 2-caprate and long-chain linear or branched mono- or polyvalent fatty alcohols, such as octyldodecanol, have proven particularly useful. Similarly, a refatting effect is attributed to the components isopropyl myristate and cetearyl octanoate.

The refatting agents are usually employed in amounts of from 0.01 to 5% by weight, preferably from 0.1 to 2% by weight, respectively based on the total agent.

For supporting their effectiveness, the disinfectants according to the invention may additionally contain further additive components with microbicidal activity. Preferably, such additive components are volatile and selected, in particular, from the group consisting of benzalkonium chloride, didecyldimethylammonium chloride, mecetronium etilsulfate, octenidine, polyhexamethylene biguanide, chlorohexidine gluconate, chlorohexidine acetate, cetrimide, cetylpyridinium chloride, hexetidine, alkylthiuronium compounds, benzyl alcohol, phenoxyethanol, phenoxypropanols, ethylhexylglycerol, undecylenic acid, 2-biphenylol, triclosan, p-chloro-m-xylenol and thymol.

In a preferred embodiment, the disinfectants according to the invention contain one or more volatile additive components with microbicidal activity in an amount of from 0.001 to 2% by weight, respectively based on the total agent.

Further, the disinfectants, which are preferably in liquid form, may contain up to 2% by weight of a solubilizer, based on the total agent. Preferably, these solubilizers are selected from the group consisting of fatty alcohol alkoxylates and/or hydrogenated castor oil.

Further, the disinfectants according to the invention may contain up to 2% by weight of denaturing agents, colorants and/or odor corrigents, based on the total agent. Denaturing agents are substances used to render alcohols, for example, ethanol, unsuitable for ingestion. Suitable denaturing agents include, for example, butan-2-one, denatonium benzoate (trade name Bitrex), diethyl phthalate. Odor corrigents are substances which at least partially conceal the inherent odor of alcohols and which, upon being applied to hands or surfaces, preferably leave a pleasant scent. In a narrower sense, odor corrigents are natural, naturally occurring synthetic and/ or artificial synthetic odorous substances or their mixtures, perfumes and/or essential oils. In a broader sense, however, odor-neutralizing substances, such as zinc ricinoleate or cyclodextrins, may also be used. The choice of the above mentioned additives is within the skill of the art and can be respectively adapted to desires and requirements without problems.

In a further preferred embodiment, the disinfectants according to the invention additionally contain an oxygen-releasing compound. It has been found that peroxygen compounds can be incorporated stably just in disinfectants according to the invention. In particular, suitable oxygen-releasing compounds include aliphatic peracids, such as peracetic acid or perpropionic acid and/or aromatic peracids, such as perbenzoic acid or monoperoxyphthalic acid and its salts, such as magnesium monoperoxyphthalate. Further suitable are glycerol monoperacetate diacetate and/or glycerol monoperacetate acetate and/or glycol peracetate acetate, which can be obtained, for example, from the reaction of peracetic acid with glycerol triacetate and/or glycerol diacetate and/or glycol diacetate. Also, monoperoxycitric acid can be readily incorporated in the agents according to the invention. The use of hydrogen peroxide is particularly preferred.

Preferably, the disinfectants according to the invention contain oxygen-releasing compounds in an amount of up to 1% by weight, based on the total agent.

In addition, the disinfectants according to the invention may contain further inorganic and organic acids. Preferably employed are organic acids, such as citric acid, lactic acid, tartaric acid, malic acid, pyroglutamic acid, gluconic acid and the corresponding glucono-8-lactone. In a preferred embodiment, the disinfectants according to the invention additionally contain one of the above mentioned acids, especially gluconic acid and/or the corresponding glucono-6-lactone.

Depending on their field of application, the disinfectants according to the invention may preferably be formulated in liquid to gel form. Low-viscous agents are preferably employed in spray applicators, because they can be readily dosed with commercially available spray heads. However, in a preferred embodiment, the agents according to the invention are in the form of a gel. Gels have an advantage in that they are readily dosed, for example, from liquid dispensers, and in addition have improved storage and shipping properties. By adding commercially available thickeners or gelling agents, the disinfectants according to the invention can be formulated as gels. Preferred are organic gelling agents of natural or synthetic origin, such as polyacrylamide or polyvinylpyrrolidone and their derivatives. Further preferred thickeners are selected from the group consisting of agar, guar gum, alginates, xanthan gum, gum arabic, locust bean gum, linseed gums, dextrans, cellulose derivatives, e.g., methylcellulose, hydroxyalkylcellulose and carboxymethylcellulose, starch fractions and derivatives, such as amylose, amylopectin and dextrins. Further, polyvinyl alcohol as well as partially saponified polyvinyl acetates and their derivatives can be preferably employed.

In a preferred embodiment, the disinfectants according to the invention have a viscosity of above 250, preferably above 500, more preferably above 1000, more preferably from 2000 to 35,000, especially from 3000 to 30,000, especially from 4000 to 25,000, advantageously from 5000 to 20,000, for example, from 6000 to 15,000, mPa·s (Brookfield viscometer LVT-II at 4 rpm and 20° C., spindle #5).

The disinfectants according to the invention are prepared by usual processes familiar to the skilled person, for example, by mixing the individual components together in any order in a mixing device.

The disinfectants according to the invention have an excellent virucidal broad-range activity and are in addition particularly skin-friendly. In an advantageous embodiment, the disinfectant according to the invention meets the recommendation by the Robert Koch Institute on the testing and declaration of effectiveness of disinfectants against viruses (Bundesgesundheitsblatt—Gesundheitsforschung—Gesundheitsschutz 2004, 42, pages 62-66), and is effective within a minute against adenovirus type 5 (strain Adenoid 75), papovavirus [simian virus 40 (SV40), strain 777], poliovirus (polio vaccination strain type I, strain LSc-2ab), and vaccinia virus (strain Elstree). In addition, it has been found that the agents according to the invention are effective against the bovine viral diarrhea virus and the feline calicivirus within 15-30 seconds. Further, the disinfectants according to the invention are effective within 1 minute in accordance with the testing standard EN 14476. In addition, it has been established that the agents according to the invention not only have a strong virucidal broad-range activity, but additionally have bactericidal activity. According to the testing standards EN 1040, EN 12054, EN 1500 and prEN 12791, the disinfectants according to the invention have proven to have bactericidal activity.

Also, the disinfectant according to the invention is suitable for killing fungi. According to the testing standard EN 1275, the disinfectants according to the invention also have fungicidal activity.

Therefore, the present invention further relates to the use of the disinfectant according to the invention as a bactericidal and/or fungicidal agent. In addition, the present invention further relates to the use of the disinfectant according to the invention for killing enveloped and non-enveloped viruses, such as adenovirus type 5 (strain Adenoid 75), papovavirus [simian virus 40 (SV40), strain 777], poliovirus (polio vaccination strain type I, strain LSc-2ab), and vaccinia virus (strain Elstree), especially for killing bovine viral diarrhea virus, rotavirus (strain WA), feline calicivirus (surrogate virus for NORO viruses), avian influenza A virus, and bovine coronavirus (surrogate virus for SARS).

In a preferred embodiment of the present invention, the disinfectants are used for the hygienic disinfection of animate surfaces, especially human or animal skin areas. The use of the disinfectants according to the invention for the disinfection of animate surfaces has proven excellent especially because the agents have a particularly good skin tolerance and additionally have a strong virucidal broad-range activity as well as fungicidal and bactericidal activity. Therefore, the agents are employed for hygienic hand disinfection, especially for hand disinfection in surgery as well as for exposure to unknown viruses. Due to their excellent skin tolerance, the agents are suitable for continuous use as hand disinfectants.

Preferably, the disinfectants according to the invention are employed commercially in hospitals, medical practices, veterinary practices, in the agricultural field (animal keeping), in the pharmaceutical and surgical fields. In addition, the agents are of course also suitable for use in food hygiene, for example, in meat processing. If needed, the agent may further be employed in the private field as an agent for prophylaxis. This is reasonable, in particular, when great virus epidemics are looming, such as by NORO viruses, SARS, bird flu etc.

Just in the clinical field, which usually has a higher exposure to viruses, the use of the disinfectants according to the invention has proven particularly suitable.

The disinfectant according to the invention is more preferably a hand disinfectant.

In a further embodiment, the present invention relates to the use of the disinfectant according to the invention for the disinfection on inanimate surfaces, especially of door handles, bedsteads, surgical instruments, hospital equipment or household articles.

The disinfectants according to the invention are preferably formulated as low-viscosity solutions. For the disinfection of larger areas or objects, the disinfectant can be provided in a container into which the objects to be disinfected are subsequently immersed. However, the disinfectants may also be applied by spraying or wiping the objects and surfaces to be disinfected. The disinfectants have proven particularly suitable, because, in contrast to conventional disinfectants, they do not leave a greasy film on the disinfected objects treated therewith. Greasy films cause an uncomfortable skin feeling on the hands and, in extreme cases, may have the effect that a firm grip is no longer ensured. When the disinfectants according to the invention are applied to inanimate surfaces, these also have the advantage that there is no formation of a greasy film on the treated surfaces.

The disinfection method can be performed very easily. According to another preferred embodiment of the present invention, the disinfection method comprises the following steps:

a) applying the disinfectant according to the invention to a contaminated surface; and b) allowing the disinfectant to act over a period sufficient to kill viruses, fungi and/or bacteria.

The disinfection method according to the invention can be handled easily by the group of persons which may be concerned, for example, hospital personnel. In a preferred embodiment of the method according to the invention, the applying is effected by spraying and/or rubbing the disinfectant onto the surface or by immersing the surface into the disinfectant. In a further preferred embodiment, the surface is human skin, especially hands. Just in the clinical and surgical fields, the use of products containing the disinfectant of the invention has proven particularly useful. Suitable products may be, for example, spray applicators or liquid dispensers which are attached, for example, in a hygiene room in which the disinfection is to be effected. Spray applicators and liquid dispensers attached in the vicinity of washing basins are of particular importance. Thus, for example, a raw preliminary cleaning of the skin areas from soils can be effected first by means of usual cleaning agents, followed by a disinfection step with the disinfectant according to the invention, for example, in which the hands are sprayed with a spray applicator, or in which the hands and/or skin areas are rubbed with the disinfectant.

In addition to spray applicators, those products in which the disinfectant according to the invention is supported on a solid support soaked or treated with the disinfectant have been found preferably useful. Preferably, the products according to the invention are impregnated or soaked sheet fabrics or impregnated or soaked papers. For example, cotton or cellulose textiles or polypropylene nonwoven fabrics can be soaked and/or impregnated with the disinfectant according to the invention and subsequently provided in a dispensing device for cloths or tissues.

The present invention is further illustrated by the following Examples without being limited thereto.

EXAMPLES

In the following examples, the results relate to tests for virucidal efficacy performed according to the RKI Virucidal Property Recommendation under the standard testing conditions, using as test viruses one or more of the following: adenovirus type 5 (strain Adenoid 75), papovavirus [simian virus 40 (SV40), strain 777], feline calicivirus, poliovirus (polio vaccination strain type I, strain LSc-2ab), vaccinia virus (strain Elstree), and to the poliovirus type 1, strain Mahoney. For the sake of clarity, the designations are abbreviated as polio, adeno, vaccinia, and papova.

Example 1

TABLE 1

Commercially available product formulation

| Formulation component | Content | Antiviral effectiveness |
|---|---|---|
| Ethanol | 52.4 g | insufficiently effective |
| Propan-1-ol | 21.0 g | against polio, thus not |
| Dexpanthenol | 0.5 g | virucidal according to RKI |
| PEG 6 caprylic capric glycerides | 1.0 g | Virucidal Property Recommendation |
| Diisopropyl adipate, allantoin, bisabolol, denaturing agent, water | q.s. 100 g | |

In Example 1, testing was performed on feline calicivirus, adeno, papova, and polio viruses, using the formulation shown in Table 1. The formulation was essentially ineffective against polio virus, and insufficiently effective against papova virus (approximately 5 minutes exposure time required to achieve 4 $\log_{10}$ reduction). Against feline calicivirus, the following activity was found.

| Organic Loading | Feline Calicivirus (exposure time for 4 $\log_{10}$ reduction) | Adenovirus (exposure time for 4 $\log_{10}$ reduction) |
|---|---|---|
| none | 5 minutes | 1 minute |
| 0.2% Bovine Serum Albumin | Not achieved within 5 minutes | 2 minutes |
| 10% Fetal Calf Serum | 1 minute | 2 minutes |

Example 2

TABLE 2

Comparative formulation with a short-chain organic acid

| Formulation component | Content | Antiviral effectiveness |
|---|---|---|
| Ethanol | 52.4 g | insufficiently effective |
| Propan-1-ol | 21.0 g | against polio, thus not |
| Citric acid | 0.5 g | virucidal according to RKI |
| Polyethylene glycol 4000 | 1.0 g | Virucidal Property Recommendation |
| Glycerol, octyldodecanol, butan-2-one, water | q.s. 100 g | |

In Example 2, testing is performed on polio virus, using the formulation shown in Table 2. Insufficient virucidal activity is found against polio virus.

Example 3

TABLE 3

Comparative formulation with diols

| Formulation component | Content | Antiviral effectiveness |
|---|---|---|
| Ethanol | 52.4 g | under the standard test |
| Propan-1-ol | 21.0 g | conditions, insufficiently |
| Citric acid | 0.5 g | effective against polio, papova |
| Propane-1,2-diol | 5.0 g | and adeno within 1 minute |

TABLE 3-continued

Comparative formulation with diols

| Formulation component | Content | Antiviral effectiveness |
|---|---|---|
| Butane-1,3-diol | 5.0 g | |
| Butan-2-one, water | q.s. 100 g | |

In Example 3, testing is performed on the indicated viruses, using the formulation shown in Table 3. Insufficient virucidal activity is found against the indicated viruses.

Example 4

TABLE 4

Comparative experiment without the use of polyalkylene glycol

| Formulation component | Content | Antiviral effectiveness |
|---|---|---|
| Ethanol | 54.1 g | under the standard test |
| Propan-1-ol | 10.0 g | conditions, insufficiently |
| Phosphoric acid | 0.7 g | effective against papova and |
| Propane-1,2-diol | 5.9 g | adeno within 1 minute |
| Butane-1,3-diol | 5.7 g | |
| Auxiliary agents, water | q.s. 100 g | |

The formulation shown in Table 4 is a commercially available product, and the indicated virucidal efficacy is that which has been reported by published literature and internet references.

Example 5

TABLE 5

Hand disinfectant according to the invention

| Formulation component | Content | Antiviral effectiveness |
|---|---|---|
| Ethanol | 52.4 g | under standard test |
| Propan-1-ol | 21.0 g | conditions, the product |
| Phosphoric acid | 0.7 g | is effective against polio, |
| Polyethylene glycol 4000 | 1.0 g | adeno, vaccinia, papova and is thus virucidal according |
| Glycerol, octyldodecanol, butan-2-one, water | q.s. 100 g | to RKI Virucidal Property Recommendation |

In Example 5, testing was performed on the indicated viruses using the formulation shown in Table 5. (The flash point of the formulation is 21° C.)

The hand disinfectant was examined at 20° C. in an undiluted form against polio, adeno, vaccinia and papova. Due to the addition of the virus suspension and the organic loads, an 80.0% test concentration resulted (standard mixture). The selected times of action were 0.5, 1.0 and 2.0 minutes.

The hand disinfectant was able in an undiluted form to achieve a titer reduction of at least 4 $\log_{10}$ steps after a time of action of one minute in all mixtures. In the examinations against polio, no virus could be detected any more after a time of action of 2 minutes. The maximally measurable titer reductions were ≥5 $\log_{10}$ steps.

The titer reductions or reduction factors mentioned mean an inactivation of ≥99.99% or ≥99.999% and thus sufficient antiviral effectiveness. It is known that the Directions of the BGA and the DVV consider that there is antiviral effectiveness if a titer reduction of ≥4 $\log_{10}$ steps can be found (inactivation ≥99.99%).

In addition, the hand disinfectant was tested as a 90.0% solution without load and in the presence of BSA (BGA/DW load) and under a high load (dirty conditions) according to EN 14476:2005. After 30 seconds, reduction factors of at least 4 $\log_{10}$ steps were found in this case too.

A formaldehyde solution, used as a control, reduced the poliovirus titer by 1.25 and 2.13 $\log_{10}$ steps after times of action of 15 and 30 minutes, respectively. After 60 and 120 minutes, the reduction factors were ≥2.75 and ≥3.13, respectively.

The formulation shown in Table 5 was also effective within 15 seconds against feline calicivirus (surrogate virus for NORO virus), bovine viral diarrhea virus (surrogate virus for hepatitis C virus), rotavirus (strain WA), bovine coronavirus (surrogate virus for SARS) and avian influenza A virus H7N1 (surrogate virus for bird flu virus H5N1).

Example 6

TABLE 6

Hand disinfectant according to the invention

| Formulation component | Content |
|---|---|
| Ethanol | 52.4 g |
| Propan-1-ol | 21.0 g |
| Phosphoric acid | 0.7 g |
| Sodium dihydrogenphosphate | 0.2 g |
| Polyethylene glycol 4000 | 1.0 g |
| Glycerol, octyldodecanol, butan-2-one, water | q.s. 100 g |

In Example 6, efficacy of the formulation shown in Table 6 is evaluated for activity against papova and adeno virus. A titer reduction of at least 4 $\log_{10}$ steps is found after one minute for each virus, indicating good virucidal efficacy.

Example 7

TABLE 7

Disinfectant for hand disinfection according to the invention

| Formulation component | Content |
|---|---|
| Ethanol | 52.4 g |
| Propan-1-ol | 21.0 g |
| Phosphoric acid | 0.4 g |
| Sodium dihydrogenphosphate | 0.3 g |
| Polyethylene glycol 4000 | 1.0 g |
| Glycerol, octyldodecanol, butan-2-one, water | q.s. 100 g |

In Example 7, efficacy of the formulation shown in Table 7 is evaluated for efficacy against feline calicivirus, adeno, and papova virus. A titer reduction of at least 4 $\log_{10}$ steps is found after one minute for feline calicivirus and adeno virus, indicating good virucidal efficacy. Exposure of papova to the formulation shows a reduction of at least 4 $\log_{10}$ steps after of 1-2 minutes.

Example 8

TABLE 8

Hand disinfectant according to the invention

| Formulation component | Content |
|---|---|
| Ethanol | 52.4 g |
| Propan-1-ol | 21.0 g |
| Phosphoric acid | 0.8 g |
| Polyethylene glycol 4000 | 1.0 g |
| Hydrogen peroxide | 0.3 g |
| Glycerol, octyldodecanol, butan-2-one, water | q.s. 100 g |

In Example 8, efficacy of the formulation shown in Table 8 was evaluated for activity against polio virus. A titer reduction of at least 4 $\log_{10}$ steps was found after one minute, indicating good virucidal efficacy.

Comparative Examples 9a and 9b

TABLE 9

Formulations without povidone-iodine

|  | Comparative Example 9a | Comparative Example 9b |
|---|---|---|
| Purified water | q.s. 100 ml | q.s. 100 g |
| Ethanol | 55.23 g | 55.70 g |
| Butan-2-one | — | 1.00 g |
| Propan-1-ol | — | 20.00 g |
| Triclosan | 0.50 g | 0.50 g |
| Propylene glycol | 0.50 g | 0.50 g |
| Benzyl alcohol | 0.35 g | 0.35 g |
| PEG 75 lanolin (50%) | 0.50 g | 0.50 g |
| PEG 400 | 6.00 g | 6.00 g |
| PEG 4000 | 2.00 g | 2.00 g |
| Phosphoric acid (85%) | 0.12 g | 0.12 g |
| Triethanolamine | 0.10 g | 0.10 g |
| Potassium iodide | 0.20 g | <0.20 g[1] |

[1]The amount was somewhat less than 0.20 g, because the potassium iodide did not dissolve completely.

Comparative Example 9a is similar to Example 9 of U.S. published application No. 2004/0146479 A1, differing mainly in that 9a did not contain povidone-iodine since this material itself has virucidal properties and thus would bias the effects to be observed. (There are also slight differences in other minor components). Comparative Example 9b was similar to 9a, differing only in solvent choice and amount of dissolved potassium iodide.

Due to the addition of the virus suspension and the interfering substance (FCS), an 80.0% test concentration resulted. The times of action were 30, 60 and 120 seconds.

Comparative Examples 9a and 9b did not cause inactivation of the poliovirus type 1 strain LSc-2ab at 20° C. (±1° C.) within the times of action tested. Thus, for example, virus titers have been established which were even above the corresponding virus controls due to measuring errors. Even after a time of action of two minutes, no titer reduction was achieved in Comparative Examples 9a and 9b. Therefore, Comparative Examples 9a and 9b were not of sufficient effectiveness against polio viruses.

In an application test of several weeks, the acceptance of formulations according to the invention was tested and rated with a positive result. The product achieved a good tolerability, even if applied frequently, for extended periods of action, and when gloves are worn. In addition, formulations of this invention typically have been found to have good storage stability under ICH conditions.

Disinfectants according to the invention may meet the conditions of testing standard EN 14476 and may find effective use against hepatitis A virus as well as against bovine parvoviruses strain Haden. In addition, they may be effective for hygienic hand disinfection according to EN 1500 within 15 seconds as well as for hand disinfection in surgery according to prEN 12791 within 1.5 minutes, and may also have fungicidal activity according to EN 1275.

Although the invention is illustrated and described herein with reference to specific embodiments, the invention is not intended to be limited to the details shown. Rather, various modifications may be made in the details within the scope and range of equivalents of the claims without departing from the invention.

The invention claimed is:

1. A virucidal disinfectant having broad-range activity, comprising:
    a) one or more acidic phosphorus compounds selected from the group consisting of phosphoric acid, diphosphoric acid, triphosphoric acid, poly-phosphoric acid of general formula $H_{n+2}P_nO_{3n+1}$, where n is an integer of from 1 to 17, cyclotri- and cyclotetra metaphosphoric acids, polymetaphosphoric acid, peroxomonophosphoric acid, peroxodiphosphoric acid, hypophosphoric acid, diphosphoric(III,IV) acid, and salts of these acids;
    b) an alcohol component selected from the group consisting of ethanol, propane-1-ol, propane-2-ol, and mixtures of any of these;
    c) one or more polyalkylene glycols;
    wherein said one or more acidic phosphorus compounds constitute from 0.2 to 1.5% by weight of the disinfectant and wherein the disinfectant does not contain povidone-iodine.

2. The disinfectant according to claim 1, wherein the alcohol component comprises ethanol and propane-1-ol.

3. The disinfectant according to claim 1, wherein the one or more acidic phosphorus compounds comprises phosphoric acid, one or more alkali metal salts of phosphoric acid, or a mixture of any of these.

4. The disinfectant according to claim 1, wherein the one or more acidic phosphorus compounds comprises phosphoric acid, sodium dihydrogenphosphate, potassium dihydrogenphosphate, or a mixture of any of these.

5. The disinfectant according to claim 1, wherein the one or more acidic phosphorus compounds comprises phosphoric acid and one or both of sodium dihydrogenphosphate and potassium dihydrogenphosphate.

6. The disinfectant according to claim 1, wherein the one or more acidic phosphorus compounds or the salts thereof constitute from 0.2 to 1.0% by weight of the disinfectant.

7. The disinfectant according to claim 1, wherein the one or more acidic phosphorus compounds constitute from 0.2 to 0.8% by weight of the disinfectant.

8. The disinfectant according to claim 1, wherein the polyalkylene glycol is etherified in one or more of the terminal hydroxy groups thereof.

9. The disinfectant according to claim 1, wherein the polyalkylene glycol comprises one or more of a polypropylene glycol, an ethylene oxide/propylene oxide block copolymer, and a polyethylene glycol.

10. The disinfectant according to claim 1, wherein the polyalkylene glycol comprises a polyethylene glycol.

11. The disinfectant according to claim 1, wherein the average molecular weight of the one or more polyalkylene glycols is in a range from 400 to 10,000.

12. The disinfectant according to claim 1, wherein the average molecular weight of the one or more polyalkylene glycols is in a range from 1000 to 8000.

13. The disinfectant according to claim 1, wherein the average molecular weight of the one or more polyalkylene glycols is in a range from 2000 to 6000.

14. The disinfectant according to claim 1, wherein the alcoholic component constitutes from 30 to 80% by weight of the disinfectant.

15. The disinfectant according to claim 1, wherein the alcoholic component constitutes from 45 to 80% by weight of the disinfectant.

16. The disinfectant according to claim 1, wherein the alcoholic component constitutes from 60 to 75% by weight of the disinfectant.

17. The disinfectant according to claim 1, wherein the disinfectant has a flash point of at least 21° C. according to DIN 51755.

18. The disinfectant according to claim 1, further comprising from 0.01 to 5% by weight of one or more skin care components selected from the group consisting of glycerol, propane-1,2-diol, butane-1,3-diol, sorbitol, dexpanthenol, allantoin, bisabolol, tocopheryl acetate, octyldodecanol, dodecanol, tetradecanol, hexadecanol, octadeca-nol, lanolin alcohol, cetearyl alcohol, cyclomethicone, dimethicone, isopropyl myristate, isopropyl palmitate, cetearylethyl hexanoate, octyl stearate, octyl octanoate, ethylhexanoic acid ethyl ester, jojoba oil, sea buckthorn oil, wool wax, paraffin oil, vaseline, heptamethylnonane/isohexadecane, cholesterol, partial glycerides, triglycerides, and mixtures of any of these.

19. The disinfectant according to claim 18, wherein the one or more skin care components constitute from 0.1 to 2% by weight of the disinfectant.

20. The disinfectant according to claim 1, further comprising from 0.001 to 2% by weight of one or more non-volatile additive components with microbicidal activity selected from the group consisting of benzalkonium chloride, didecyldimethylammonium chloride, mecetronium etilsulfate, octenidine, polyhexamethylene biguanide, chlorohexidine gluconate, chlorohexidine acetate, cetrimide, cetylpyridinium chloride, hexetidine, alkylthiuronium compounds, benzyl alcohol, phenoxyethanol, phenoxypropanols, ethylhexylglycerol, undecylenic acid, 2-biphenylol, triclosan, p-chlorom-xylenol, thymol, and mixtures of any of these.

21. The disinfectant according to claim 1, further comprising up to 2% by weight of a solubilizer selected from the group consisting of hydrogenated castor oil, fatty alcohol alkoxylates, and mixtures of these.

22. The disinfectant according to claim 1, further comprising up to 2% by weight of one or more denaturing agents, colorants, odor corrigents, or a mixture of any of these.

23. The disinfectant according to claim 1, further comprising an oxygen-releasing compound.

24. The disinfectant according to claim 23, wherein the oxygen-releasing compound comprises hydrogen peroxide.

25. The disinfectant according to claim 23, wherein the oxygen-releasing compound comprises up to 1.0% by weight of the disinfectant.

26. The disinfectant according to claim 1, further comprising one or more refatting agents.

27. The disinfectant according to claim 1, wherein the disinfectant is in the form of a gel.

28. The disinfectant according to claim 1, said disinfectant being effective within a minute against adenovirus type 5 (strain Adenoid 75), papovavirus [simian virus 40 (SV40), strain 777], poliovirus (polio vaccination strain type I, strain LSc-2ab), and vaccinia virus (strain Elstree).

29. A product comprising a disinfectant according to claim 1 and means for dispensing the disinfectant.

30. The product according to claim 29, wherein the product comprises a solid support soaked or treated with the disinfectant.

31. The product according to claim 30, wherein the product comprises an impregnated or soaked sheet fabric, an impregnated or soaked nonwoven plastic fabric, impregnated or soaked paper, or a combination of these.

* * * * *